United States Patent
Soza

(10) Patent No.: US 11,574,743 B1
(45) Date of Patent: Feb. 7, 2023

(54) CUSTOMIZABLE COMMUNICATION PLATFORM

(71) Applicant: CAREMINDR CORPORATION, Los Gatos, CA (US)

(72) Inventor: Harry Raymond Soza, San Jose, CA (US)

(73) Assignee: CAREMINDR CORPORATION, Los Gatos, CA (US)

( * ) Notice: Subject to any disclaimer, the term of this patent is extended or adjusted under 35 U.S.C. 154(b) by 906 days.

(21) Appl. No.: 16/233,872

(22) Filed: Dec. 27, 2018

Related U.S. Application Data

(60) Provisional application No. 62/615,259, filed on Jan. 9, 2018, provisional application No. 62/712,557, filed on Jul. 31, 2018, provisional application No. 62/771,919, filed on Nov. 27, 2018.

(51) Int. Cl.
*G16H 80/00* (2018.01)
*G16H 50/20* (2018.01)

(52) U.S. Cl.
CPC .............. *G16H 80/00* (2018.01); *G16H 50/20* (2018.01)

(58) Field of Classification Search
CPC ................................ G16H 80/00; G16H 50/20
USPC .......................................................... 705/2–3
See application file for complete search history.

(56) References Cited

U.S. PATENT DOCUMENTS

| | | |
|---|---|---|
| 8,577,716 B2 | 11/2013 | Bernick et al. |
| 2008/0262872 A1 | 10/2008 | Perry et al. |
| 2009/0105550 A1 | 4/2009 | Rothman et al. |
| 2013/0054467 A1 | 2/2013 | Dala et al. |
| 2013/0073306 A1* | 3/2013 | Shlain ................... G16H 10/20 705/2 |
| 2013/0237869 A1 | 9/2013 | John et al. |
| 2014/0088985 A1 | 3/2014 | Grant et al. |
| 2015/0112722 A1 | 4/2015 | Dees et al. |
| 2015/0302150 A1 | 10/2015 | Mazar et al. |
| 2015/0310455 A1 | 10/2015 | Vinals |
| 2015/0370980 A1 | 12/2015 | Sun |
| 2017/0109479 A1* | 4/2017 | Vemireddy ............ G06Q 10/00 |
| 2017/0124276 A1 | 5/2017 | Tee |
| 2017/0160904 A1* | 6/2017 | Tene ..................... G06Q 10/107 |

(Continued)

FOREIGN PATENT DOCUMENTS

WO  WO-2013040459 A2 *  3/2013  ............. G06Q 10/06

OTHER PUBLICATIONS

Alpert et al., Patient-centered communication in digital medical encounters, Patient Educ Couns, 2017;100(10):1852-1858. doi: 10.1016/j.pec.2017.04.019 (Year: 2017).*

(Continued)

*Primary Examiner* — Joy Chng

(57) ABSTRACT

Processing patient information and other treatment plan information may require access to a patient profile and other third parties involved in the patient treatment plan. One example method includes selecting a treatment plan for a patient comprising a set of treatment information, linking an application identifier and a T-code identifier to the treatment plan, launching a treatment plan application, retrieving the set of treatment information, populating the treatment plan application with the set of treatment information, triggering a message dispatch in accordance with the treatment plan, the message dispatch including a query to a health related issue to determine a patient status and receiving a patient response to the message.

19 Claims, 13 Drawing Sheets

(56) References Cited

U.S. PATENT DOCUMENTS

| | | |
|---|---|---|
| 2017/0172413 A1 | 6/2017 | Chakravarthy et al. |
| 2017/0228517 A1 | 8/2017 | Saliman et al. |
| 2017/0262604 A1 | 9/2017 | Francois |
| 2017/0293700 A1 | 10/2017 | Bazaz et al. |
| 2017/0372029 A1 | 12/2017 | Saliman et al. |
| 2018/0075219 A1 | 3/2018 | Klein et al. |
| 2019/0019578 A1 | 1/2019 | Vaccaro |
| 2019/0189258 A1 | 6/2019 | Barrett et al. |
| 2020/0258609 A1 | 8/2020 | McMaster et al. |
| 2021/0050098 A1 | 2/2021 | Sterner et al. |
| 2022/0270733 A1 | 8/2022 | Hagen et al. |

OTHER PUBLICATIONS

Heath, Clinicians Need To Reframe Their Clinical Workflows To Successfully Implement Patient Portal Secure Messaging, Patient Engagement Hit, Sep. 19, 2017, https://patientengagementhit.com/news/top-tips-for-successful-patient-portal-secure-messaging (Year: 2017).*

* cited by examiner

100

400

430

Example: Journey – Message Set

App ID / Ofc ID / OVDT / PR# / JID / Start Date / T-Code / on-off

>> The T-Code is stored in the Patient's device & reported at each App "open"

| CAT | JID + MSG # | MSG DAY | TEXT | RS DELAY | LINK TO RESPONSE PAGE |
|---|---|---|---|---|---|
| OPTH | 201.00 | 0 | Your Care Journey: OPTH-201 - starts today ! (CLICK) | 0 | https://Opth201-Info-Description |
| OPTH | 201.01 | 1 | Use Eye drops 4x per day (CLICK) | 1 | https://ourewards.box.com/s/s8au5rmlpi |
| OPTH | 201.02 | 5 | Eye-Dr appointment in two days - please confirm (CLICK) | 2 | http://simedicalgroup.com/?page_id=102 |
| OPTH | 201.03 | 14 | Use Eye drops 2x per day (CLICK) | 2 | https://ourewards.box.com/s/s8au5rmlpi |
| OPTH | 201.04 | 21 | Perform a vision self-test (CLICK) | 1 | https://ourewards.box.com/s/s8au5rmlpi |
| OPTH | 201.05 | 25 | Renew 30 day Rx - eye drops (CLICK) | 1 | https://ourewards.box.com/s/s8au5rmlpi |
| OPTH | 201.06 | 28 | Use Eye drops 1x per day (CLICK) | 2 | https://ourewards.box.com/s/s8au5rmlpi |
| OPTH | 201.07 | 35 | Complete Eye-Dr Patient Report (CLICK) | 2 | https://ourewards.box.com/s/s8au5rmlpi |
| OPTH | 201.08 | 35 | Check in report | 2 | https://ourewards.box.com/s/s8au5rmlpi |
| OPTH | 201.09 | 53 | 2 month Eye-Dr appointment next week - pls confirm (CLICK) | 2 | http://simedicalgroup.com/?page_id=102 |
| OPTH | 201.99 | 60 | END | 0 | END |

Journey Overview – visible via app

CUSTOMIZABLE COMMUNICATION PLATFORM

TECHNICAL FIELD OF THE APPLICATION

This application relates to a customizable communication platform and more particularly to providing customized communication to a user device by integrating various personal records with an ongoing communication regiment.

BACKGROUND OF THE APPLICATION

Conventionally, the approach to providing users with ongoing communications regarding a plan or other repetitive course of action may leave the majority of the work to the user. The smartphone and other personal computing devices are everywhere and are not being properly utilized when offering users with options for maintaining a course of treatment or a set of goals. The lack of action taken by the professional service provider and/or the user can lead to personal health problems and lost revenue for providers, insurers, etc., as well as the users.

SUMMARY OF THE APPLICATION

An example embodiment of the present application provides at least a method that includes at least one of selecting a treatment plan for a patient comprising a set of treatment information, linking an application identifier and a T-code identifier to the treatment plan, launching a treatment plan application, retrieving the set of treatment information, populating the treatment plan application with the set of treatment information, triggering a message dispatch in accordance with the treatment plan, the message dispatch including a query to a health related issue to determine a patient status and receiving a patient response to the message.

Another example embodiment of the present application provides at least non-transitory computer readable medium comprising instructions that, when read by a processor, cause the processor to perform at least one of selecting a treatment plan for a patient comprising a set of treatment information, linking an application identifier and a T-code identifier to the treatment plan, launching a treatment plan application, retrieving the set of treatment information, populating the treatment plan application with the set of treatment information, triggering a message dispatch in accordance with the treatment plan, the message dispatch including a query to a health related issue to determine a patient status and receiving a patient response to the message.

A further example embodiment of the present application provides at least a system, comprising at least one cloud based processor, and at least one memory electrically coupled to the at least one processor and storing an application, the processor at least one of selects a treatment plan for a patient comprising a set of treatment information, links an application identifier and a T-code identifier to the treatment plan, launches a treatment plan application, retrieves the set of treatment information, populates the treatment plan application with the set of treatment information, triggers a message dispatch in accordance with the treatment plan, the message dispatch including a query to a health related issue to determine a patient status and receives a patient response to the message.

BRIEF DESCRIPTION OF THE DRAWINGS

FIG. 4B illustrates an example database entry for the new course of treatment according to example embodiments.

DETAILED DESCRIPTION OF THE APPLICATION

It will be readily understood that the components of the present application, as generally described and illustrated in the figures herein, may be arranged and designed in a wide variety of different configurations. Thus, the following detailed description of the embodiments of a method, apparatus, and system, as represented in the attached figures, is not intended to limit the scope of the application as claimed, but is merely representative of selected embodiments of the application.

The features, structures, or characteristics of the application described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment of the present application. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

Figure 1:
FIG. 1 illustrates an example of the integrated application platform according to example embodiments.

FIG. 1 illustrates an example of the integrated application platform according to example embodiments. Referring to FIG. 1, the configuration 100 includes a menu user interface, a home user interface and a set of option tiles for accessing third party resources, such as test results, emergency concerns, pharmacy information, etc.

Figure 2:
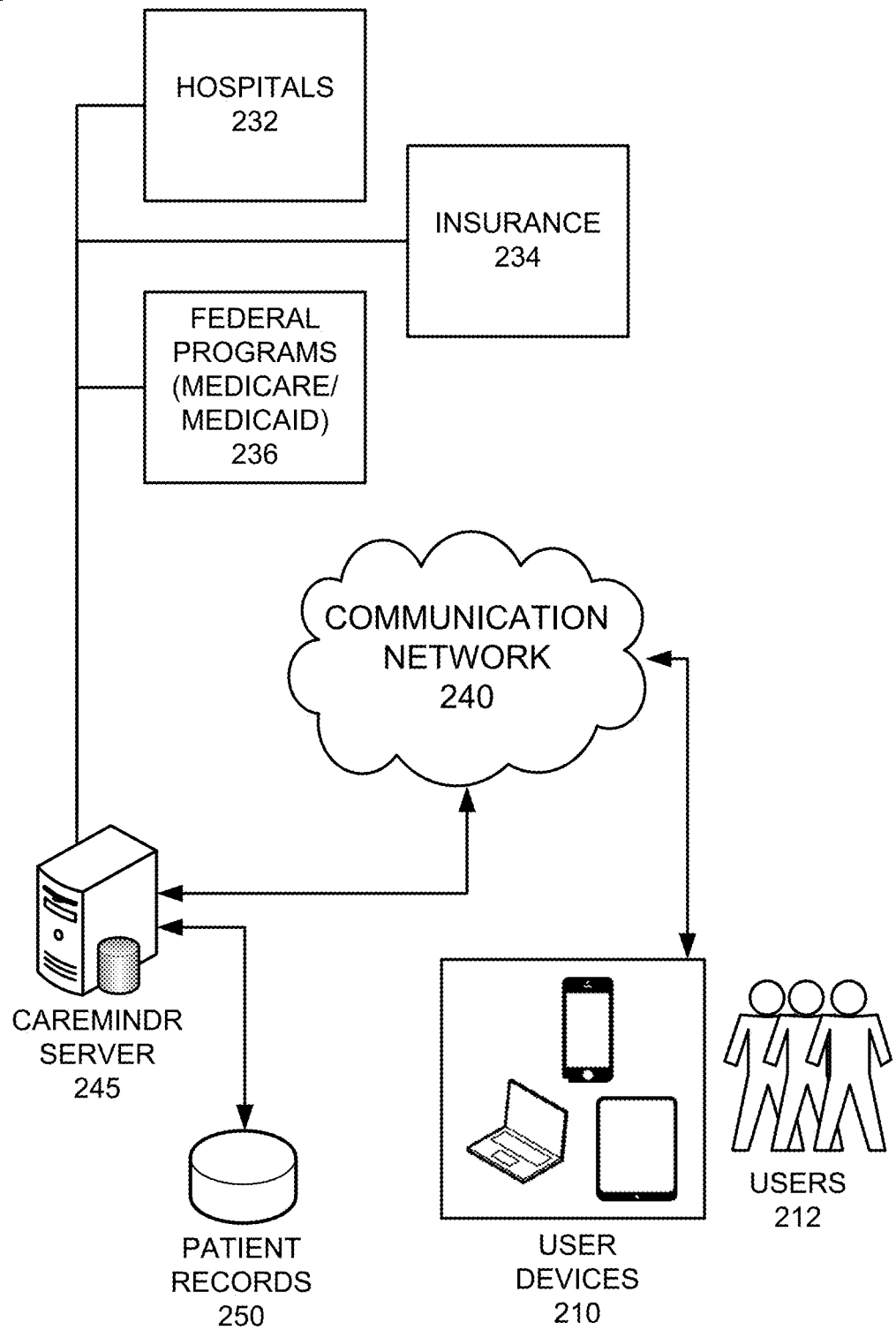
FIG. 2 illustrates a network configuration of the third party participants of the integrated application according to example embodiments.

FIG. 2 illustrates a network configuration of the third party participants of the integrated application according to example embodiments. Referring to FIG. 2, the network includes a central server 245 with patient records 250. The information needed to provide treatment plans and other integrated services may require access to hospital and other provider services 232, insurance company information 234, drug providers, federal program administrators 236, etc. The information may be incorporated into any treatment plan or other integrated service model accessed by a user device 210 operated by a user 212. The servers and third party modules may operate on-site or in a cloud network managed by the providers.

Examples of treatment plans and other objectives may include a care management service for assessment of patient medical needs. The system and application may ensure timely receipt of all recommended treatment actions, drugs, third party services and over a designated period of time. Also, referrals to other providers and additional services may provide emergency visits, discharge instructions, nursing facility operations, and home health care functions. In operation, the procedure may begin with the medical treatment provider creating a treatment plan or 'journey' for each patient. Each journey is generally for a single chronic condition or objective. One patient may have multiple journeys integrated into a single application. Also, the journeys may originate from various different providers and service entities.

Figure 3:
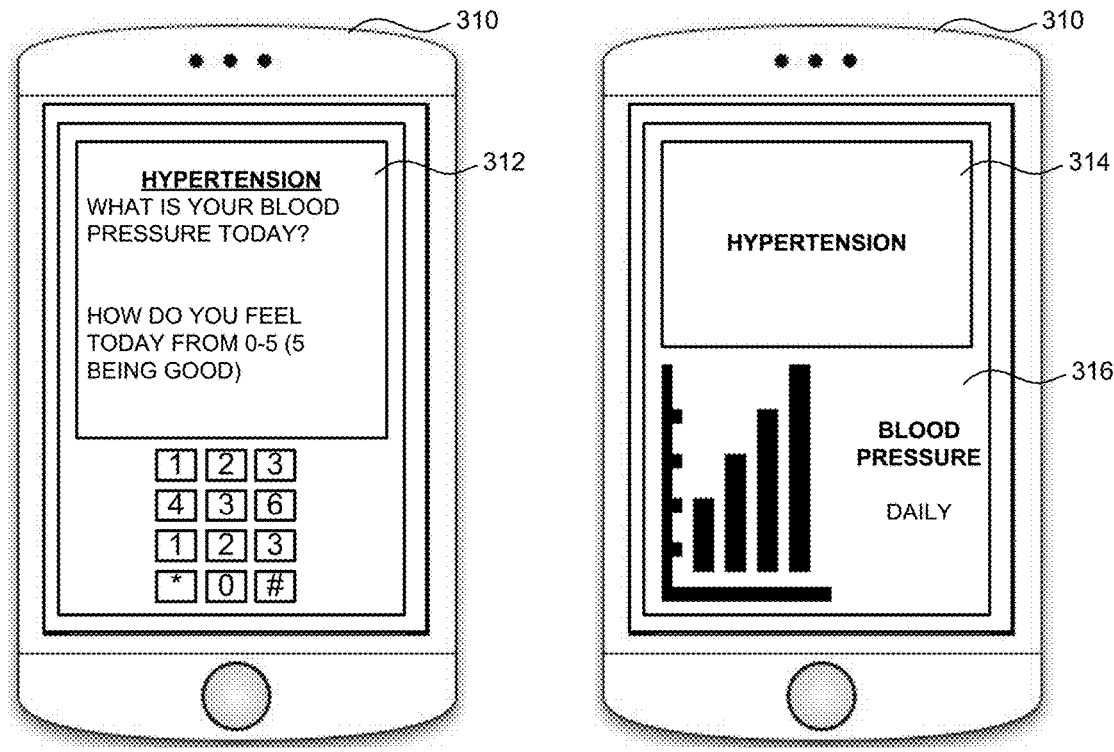
FIG. 3 illustrates a user smartphone interface of an example treatment plan according to example embodiments.

FIG. 3 illustrates a user smartphone interface of an example treatment plan according to example embodiments. Referring to FIG. 3, the journey for "hypertension" may have been created by a patient doctor and may include an interface 300 with a smartphone device 310 and a screen option configuration providing a set of questions 312, information about the treatment, reminders and other functions. The example in FIG. 3 provides for a set of questions 312 and a journey topic 314 along with a graph of blood pressure records 316 as measured over time from various interactions.

Figure 4A:
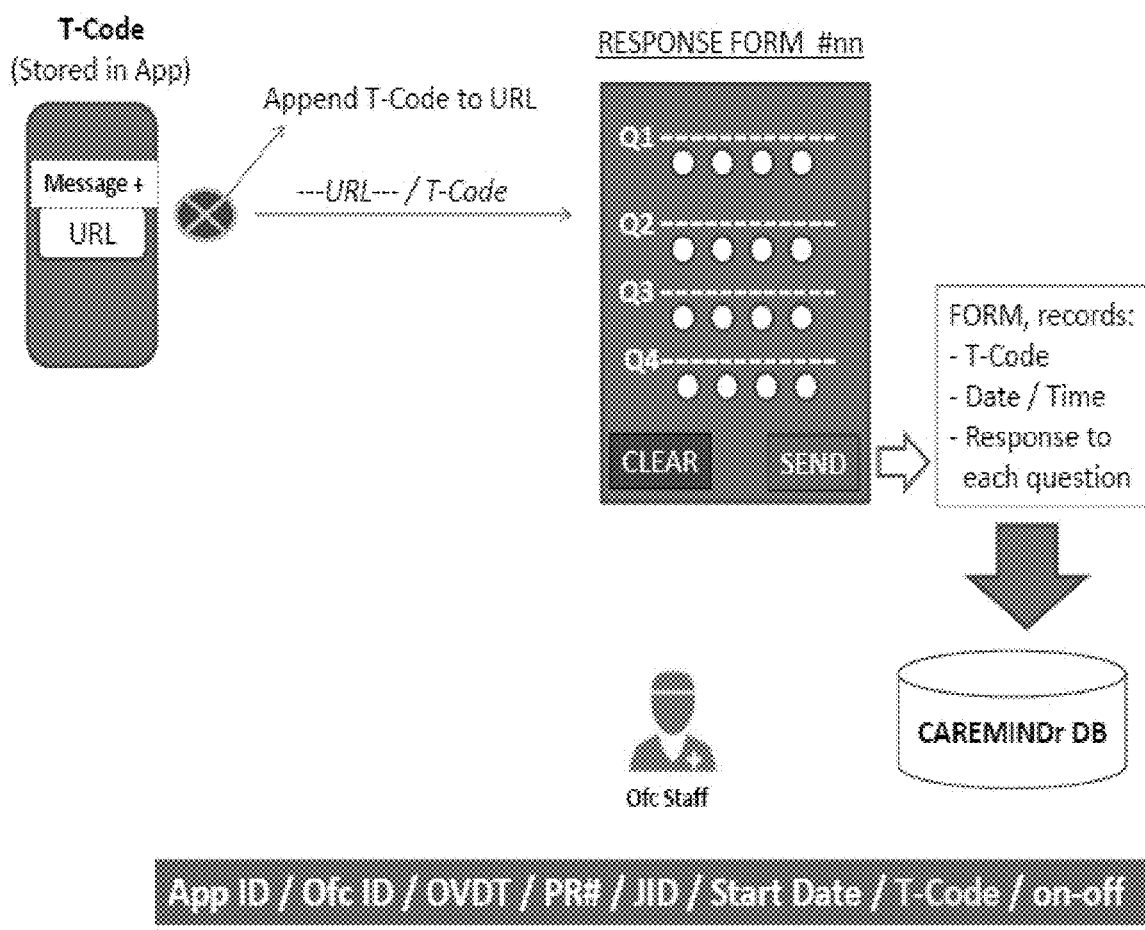
FIG. 4A illustrates an example setup configuration for a new course of treatment according to example embodiments.

FIG. 4A illustrates an example setup configuration for a new course of treatment according to example embodiments. Referring to FIG. 4A, the illustration 400 includes the basic setup functions of linking a particular journey T-code (unique code) to the message and/or universal resource link (URL) to link the application of the user to a customized template, such as a response form, questionnaire, etc. The T-code, date, time, response, and other records for each instance may be stored in a patient record managed by the application system database.

FIG. 4B illustrates an example database entry for the new course of treatment according to example embodiments. Referring to FIG. 4B, the example configuration 430 includes a database entry of messages which are organized by a category, in this case ophthalmology, and with a message content, including a link to a response page. The context and add-ons of a particular message may be customized based on a preferred layout or a default layout.

Figure 4C:
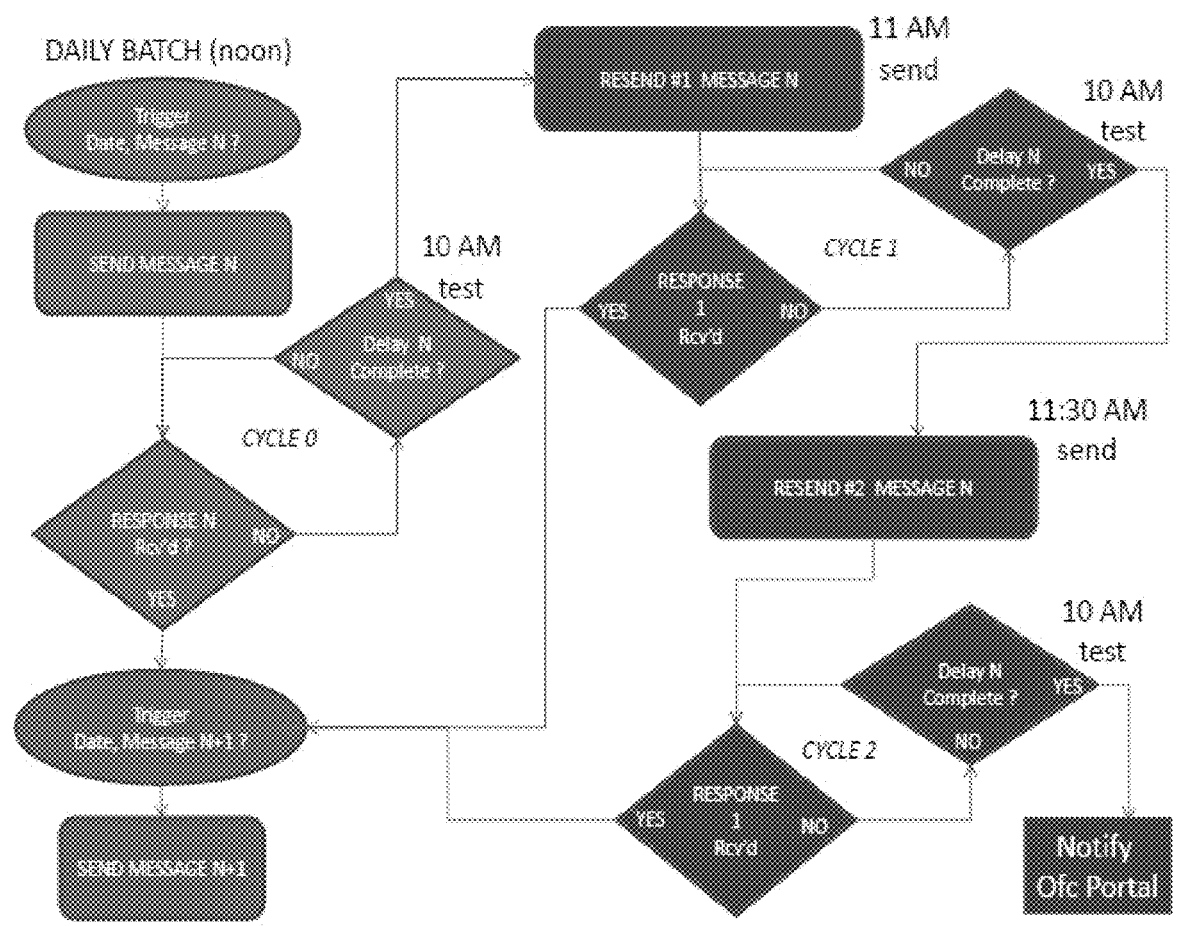
FIG. 4C illustrates a flow diagram configuration for the new course of treatment according to example embodiments.

FIG. 4C illustrates a flow diagram 440 configuration for the new course of treatment according to example embodiments. Referring to FIG. 4C, the flow diagram includes a daily batch of messages which are setup to be delivered to one or more assigned patients. The process begins with a trigger to send a message, such as a matured date or time. The process then continues to deliver additional messages once confirmation of delivery is made. If the message is delayed or the response required is not received, the message may be resent as a late message requiring immediate attention. The process may continue to cycle to identify whether any messages are outstanding or have not been confirmed.

Figure 4D:
FIG. 4D illustrates an example list of messages for the ongoing course of treatment according to example embodiments.
Figure 4E:
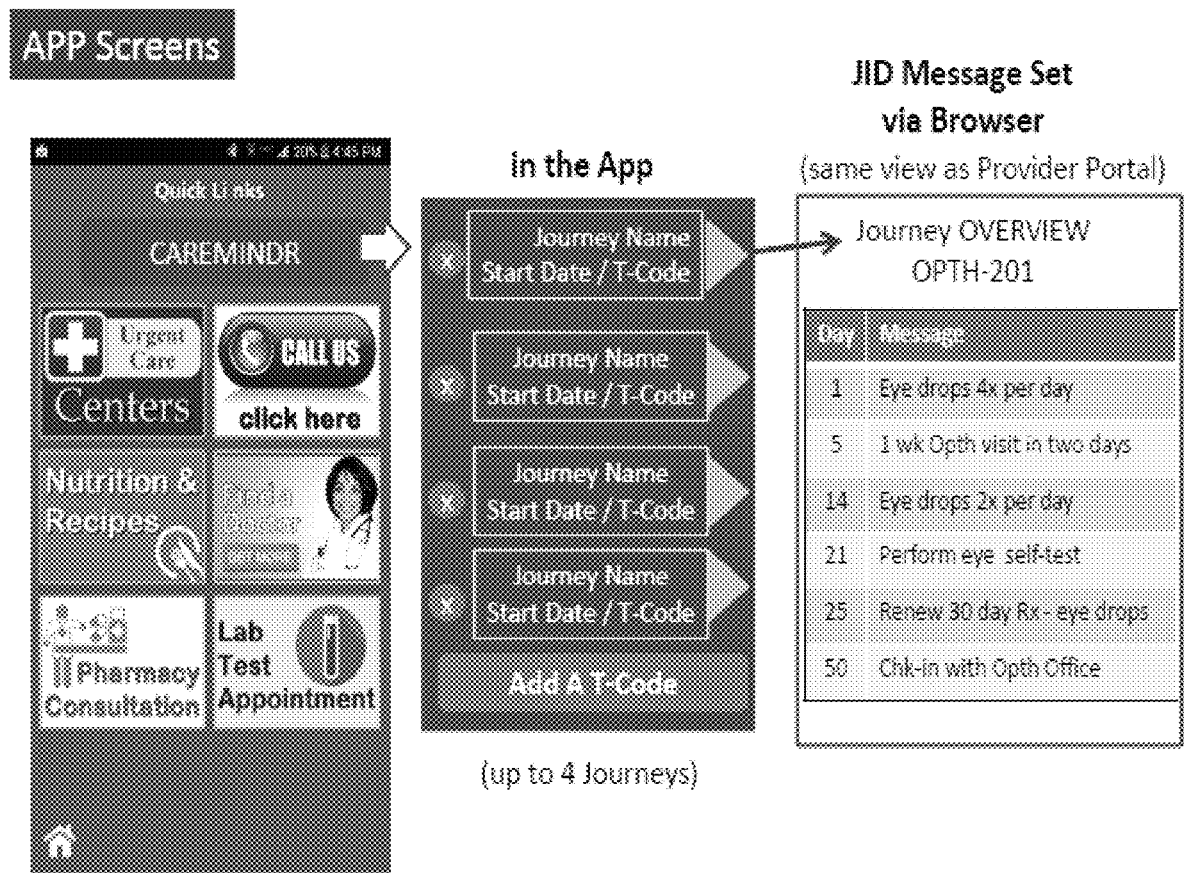
FIG. 4E illustrates an example setup configuration for various courses of treatment according to example embodiments.

FIG. 4D illustrates an example list of messages for the ongoing course of treatment according to example embodiments. Referring to FIG. 4D, in this illustration 450, the various messages intended for a particular patient are illustrated by date. FIG. 4E illustrates an example setup configuration for various courses of treatment according to example embodiments. Referring to FIG. 4E, the configuration 460 includes a menu of options along with a set of potential journeys the user may be assigned to manage the ongoing health care treatment plans for that user. The overview of treatment options and dates are included for reference purposes.

Figure 4F:
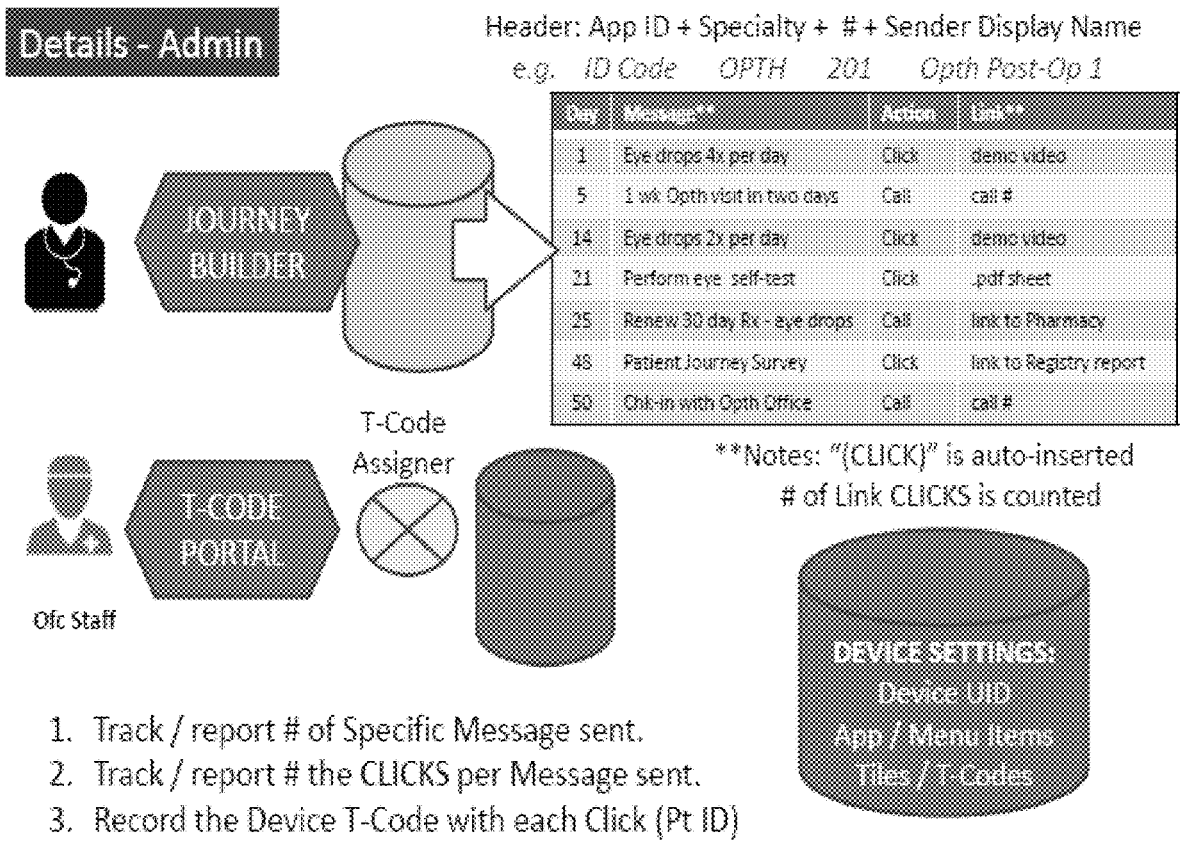
FIG. 4F illustrates an example set of details of an ongoing course of treatment according to example embodiments.

FIG. 4F illustrates an example set of details of an ongoing course of treatment according to example embodiments. Referring to FIG. 4F, the details of the administrator are shown to include a journey builder function based on certain parameters, such as an identification code, specialty, a number and a sender name. The number of messages, responses and actions are recorded to demonstrate the user's interaction with the application and the specific treatment plan(s).

Figure 4G:
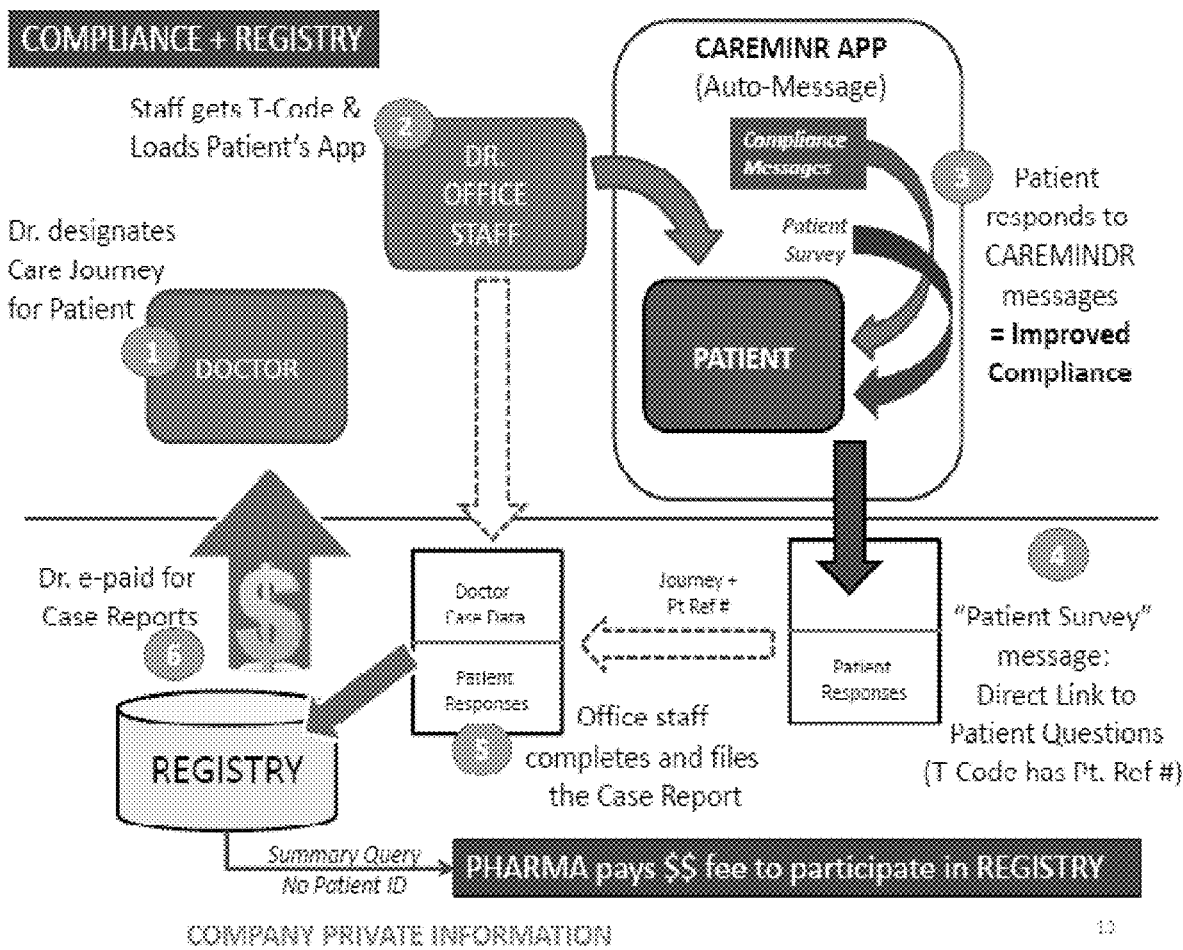
FIG. 4G illustrates an example network configuration of the various third parties involved in the application operation and compliance according to example embodiments.

FIG. 4G illustrates an example network configuration of the various third parties involved in the application operation and compliance according to example embodiments. Referring to FIG. 4G, the large-scale network of communications among the integrated platform 480 demonstrates the process initiating with the doctor's office establishing a journey for the patient and assigning a T-code. The patient's responses are identified along with links and references to third party message links and other information sources.

Figure 5:
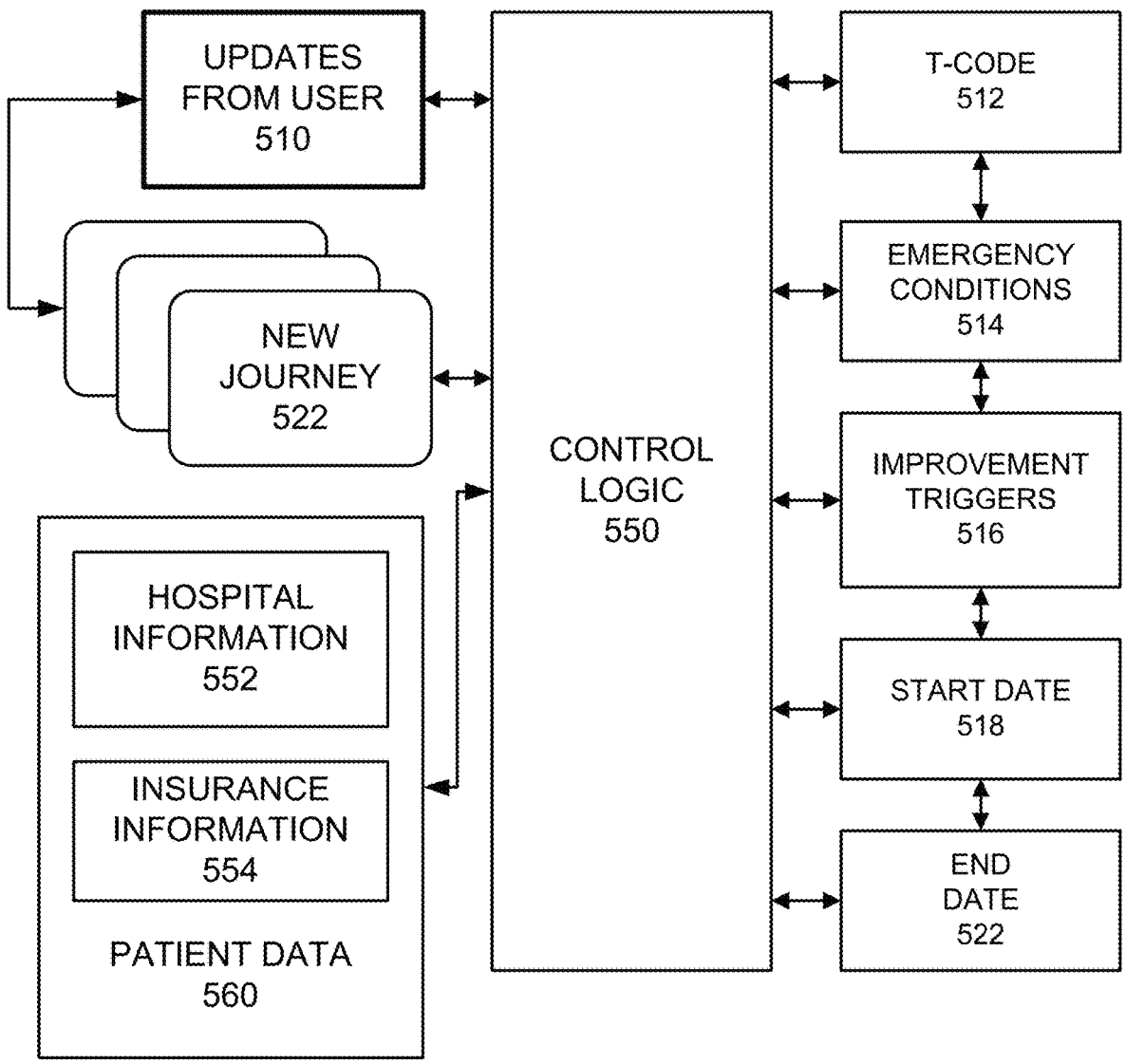
FIG. 5 illustrates a logic module configured to process the input and output parameters of the application according to example embodiments.

FIG. 5 illustrates a logic module configured to process the input and output parameters of the application according to example embodiments. Referring to FIG. 5, the control logic platform 500 includes a control logic unit 555, such as a processor or other processing entity that may receive updates from a user 510, new journey information 522 and/or patient data 560 including hospital 552, insurance 554, and other information. The logic may be configured to identify and link the assigned T-code 512, emergency conditions 514, improvement triggers 516 for optimal changes to the treatment plan, along with dates 518 and new journey information 522 to perform the treatment plan.

In addition, while the term "message" has been used in the description of embodiments of the present application, the application may be applied to many types of network data, such as, packet, frame, datagram, etc. For purposes of this application, the term "message" also includes packet, frame, datagram, and any equivalents thereof. Furthermore, while certain types of messages and signaling are depicted in exemplary embodiments of the application, the application is not limited to a certain type of message, and the application is not limited to a certain type of signaling.

According to example embodiments, a user device, such as a smartphone, cellular phone, tablet device, laptop or other computing device with a memory and processor, may communicate with another computing device and/or a server to provide an integrated communication platform.

Example embodiments provide a computer system programmed to use automated messaging from medical offices to specific patients. The application is not limited to medical procedures and functions and may be used with other configurations for various purposes and services benefitting the end user. Example embodiments include three main computer systems, which work together in an integrated manner including a management platform that controls set-up, functionality, activity reporting, and messaging credentials for the users. An administrative platform which the doctor and doctor's office can access via the internet, and a mobile application that a patient can download into a mobile computer device such as a smartphone or tablet.

The integrated platform provides a way of checking-in with a patient at prescribed intervals during times between office visits and when undergoing certain treatment that the doctor is providing or overseeing for the patient. The patient dialog may gather relevant information about the status of the patient's conditions or recovery and can be modified or tailored to specifically meet the dialog requirements of the treating physician. Once initiated by the doctor's office, the application operates in an autonomous manner by delivering messages to the patient to prompt responses if needed. The application functions are monitored to assure that the patient replies to the information requests from the doctor, otherwise a no-response alert is sent to the doctor's office. The interactions are recorded and time-stamped, providing an auditable record of the dialog, suitable for insurance billing purposes. The application can also support parametric information from devices that measure certain body functions, such as diabetes glucometers, or blood pressure cuffs, or any sensory readable health care metric. The application may also create a longitudinal record of information for the patient to illustrate week-to-week trends.

The operations of a method or algorithm described in connection with the embodiments disclosed herein may be embodied directly in hardware, in a computer program executed by a processor, or in a combination of the two. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example, FIG. 6 illustrates an example network entity 600, which may represent any of the above-described network components of the other figures.

Figure 6:
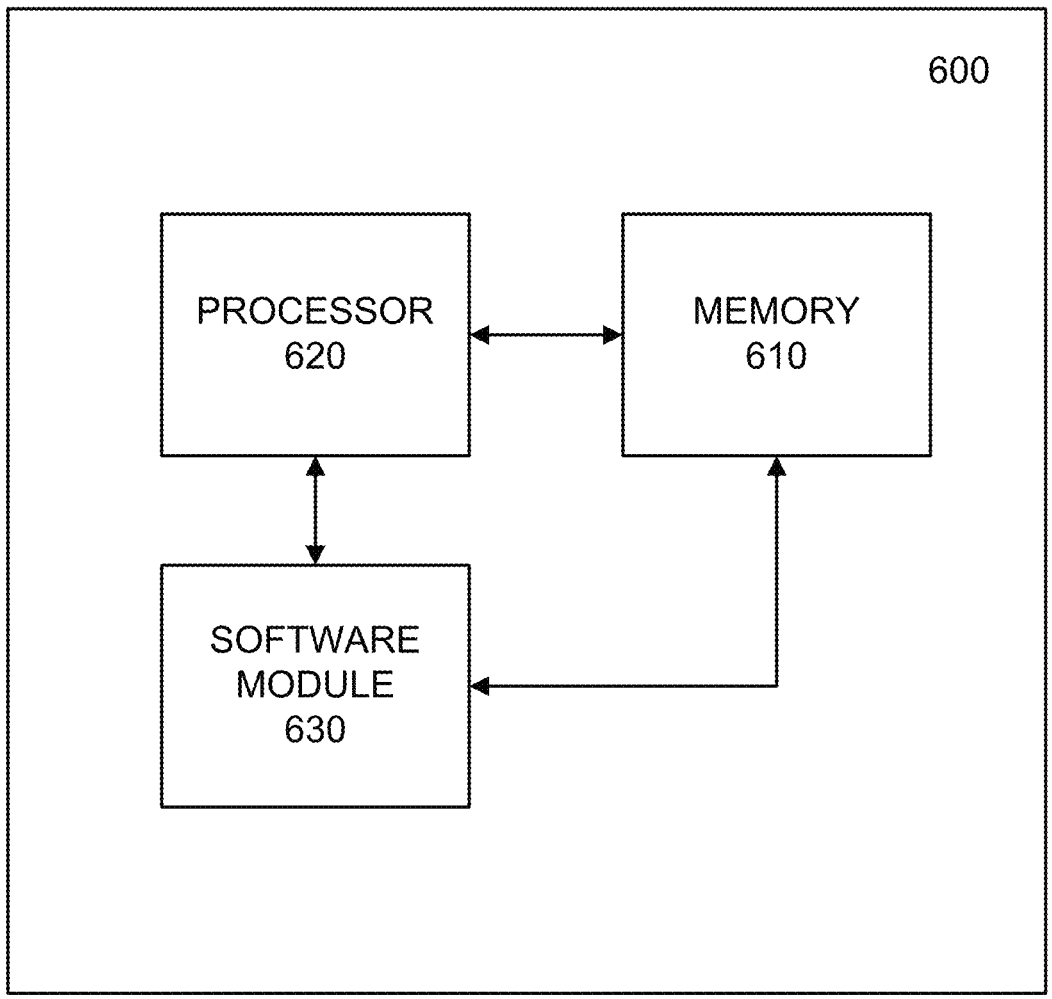
FIG. 6 illustrates an example network entity device configured to store instructions, software, and corresponding hardware for executing the same, according to example embodiments of the present application.

As illustrated in FIG. 6, a memory 610 and a processor 620 may be discrete components of the network entity 600 that are used to execute an application or set of operations. The application may be coded in software in a computer language understood by the processor 620, and stored in a computer readable medium, such as, the memory 610. The computer readable medium may be a non-transitory computer readable medium that includes tangible hardware components in addition to software stored in memory. Furthermore, a software module 630 may be another discrete entity that is part of the network entity 600, and which contains software instructions that may be executed by the processor 620. In addition to the above noted components of the network entity 600, the network entity 600 may also have a transmitter and receiver pair configured to receive and transmit communication signals (not shown).

Figure 7:
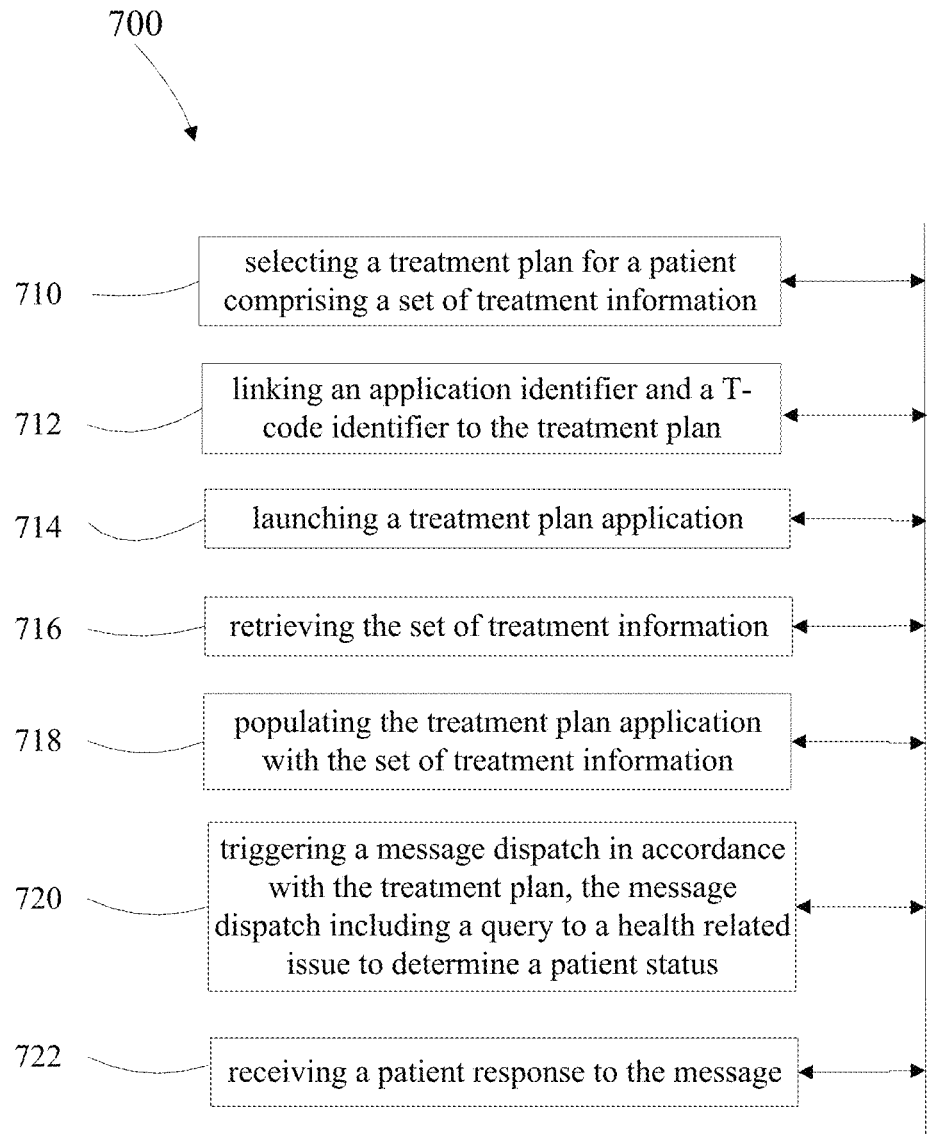
FIG. 7 illustrates a first method, according to example embodiments of the present application.

A first example method shown in FIG. 7, 700, may include, selecting 710 a treatment plan for a patient comprising a set of treatment information, linking 712 an application identifier and a T-code identifier to the treatment plan and launching 714 a treatment plan application. The method further includes retrieving 716 the set of treatment information, populating 718 the treatment plan application with the set of treatment information and triggering 720 a message dispatch in accordance with the treatment plan. The message dispatch includes a query to a health related issue to determine a patient status and the system receives 722 a patient response to the message.

With respect to the timing of patient responses, the first example method may also include, awaiting the patient response to the message for a late response duration and categorizing the patient response if the patient response is received within the late response duration. If the patient response is not received within the late response duration the method further comprises sending a duplicate message and flagging the patient response as non-responsive if the patient response to the duplicate message is not received within a second late response duration.

The timing of the message dispatches associated with the treatment plan is partly governed by a trigger table. The method may include loading the trigger table having a set of trigger dates based on the treatment plan where the message dispatch is sent according to the set of trigger dates. The method may further include receiving a message start date and receiving an initialization message from a patient mobile device to initiate the treatment plan and to initialize the set of trigger dates in the trigger table.

Although an exemplary embodiment of the system, method, and computer readable medium of the present application has been illustrated in the accompanied drawings and described in the foregoing detailed description, it will be understood that the application is not limited to the embodiments disclosed, but is capable of numerous rearrangements, modifications, and substitutions without departing from the spirit or scope of the application as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way, but is intended to provide one example of many embodiments of the present application. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed, but is merely representative of selected embodiments of the application.

One having ordinary skill in the art will readily understand that the application as discussed above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent, while remaining within the spirit and scope of the application. In order to determine the metes and bounds of the application, therefore, reference should be made to the appended claims.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. A method, comprising:
   storing a software application comprising a plurality of journeys corresponding to a plurality of treatment plans incorporated therein;
   receiving a request for a treatment plan for a patient comprising a set of treatment information, the request comprising a uniform resource locator (URL) and being provided from the software application on a user device;
   identify a unique identifier of a customized message template appended to an end of the URL;
   identifying a journey corresponding to the unique identifier;
   triggering a message dispatch to the software application on the user device in accordance with the journey corresponding to the unique identifier, the triggering comprising customizing a layout and content within each message being dispatched based on the customized message template linked to the unique identifier appended to the end of the URL and transmitting the customized message to the software application on the user device; and
   receiving a patient response from the software application on the user device.

2. The method of claim 1, further comprising loading a trigger table having a set of trigger dates based on the journey and triggering the message dispatch responsive to the set of trigger dates in the trigger table.

3. The method of claim 2, further comprising receiving a message start date and receiving an initialization message from a patient mobile device to initiate the journey and to initialize the set of trigger dates in the trigger table.

4. The method of claim 1, further comprising:
   awaiting the patient response for a late response duration;
   categorizing the patient response if the patient response is received within the late response duration;
   sending a duplicate message if the patient response is not received within the late response duration; and
   flagging the patient response as non-responsive if the patient response to the duplicate message is not received within a second late response duration.

5. The method of claim 1, further comprising entering a database entry of the message organized by a category.

6. The method of claim 1, wherein the linking further comprises linking the URL of the software application to at least one of a response form and a questionnaire.

7. The method of claim 1, further comprising receiving parametric device information of patient body functions.

8. The method of claim 1, wherein the patient response may be tracked in a longitudinal record.

9. The method of claim 1, further comprising:
   receiving a medical office identification;
   receiving a patient reference number; and
   receiving an office visit timestamp.

10. The method of claim 1, further comprising at least one of creating the journey and modifying the journey.

11. The method of claim 1, further comprising storing the unique identifier, a timestamp and the patient response to an auditable patient record.

12. A non-transitory computer readable medium comprising instructions that, when read by a processor, cause the processor to perform:
   storing a software application comprising a plurality of journeys corresponding to a plurality of treatment plans incorporated therein;
   receiving a request for a treatment plan for a patient comprising a set of treatment information, the request comprising a uniform resource locator (URL) and being provided from the software application on a user device;

identifying a unique identifier of a customized message template appended to an end of the URL;

identifying a journey corresponding to the unique identifier;

triggering a message dispatch to the software application on the user device in accordance with the journey corresponding to the unique identifier, the triggering comprising customizing a layout and content within each message being dispatched based on the customized message template linked to the unique identifier appended to the end of the URL and transmitting the customized message to the software application on the user device; and receiving a patient response from the software application on the user device.

13. The non-transitory computer readable medium of claim 12, further comprising loading a trigger table having a set of trigger dates based on the journey and triggering the message dispatch responsive to the set of trigger dates in the trigger table.

14. The non-transitory computer readable medium of claim 13, further comprising receiving a message start date and receiving an initialization message from a patient mobile device to initiate the journey and to initialize the set of trigger dates in the trigger table.

15. The non-transitory computer readable medium of claim 12, further comprising:

awaiting the patient response for a late response duration;

categorizing the patient response if the patient response is received within the late response duration;

sending a duplicate message if the patient response is not received within the late response duration; and flagging the patient response as non-responsive if the patient response to the duplicate message is not received within a second late response duration.

16. A system, comprising:

a memory configured to store a software application comprising a plurality of journeys corresponding to a plurality of treatment plans incorporated therein; and a processor configured to:

receive a request for a treatment plan for a patient comprising a set of treatment information, the request comprising a uniform resource locator (URL) and being provided from flail the software application on a user device;

identify a unique identifier of a customized message template appended to an end of the URL;

identify a journey corresponding to the unique identifier;

trigger a message dispatch to the software application on the user device in accordance with the journey corresponding to the unique identifier, wherein the processor is configured to customize a layout and content within each message that is dispatched based on the customized message template linked to the unique identifier appended to the end of the URL and transmit the customized message to the software application on the user device; and receives a patient response to the message.

17. The system of claim 16, wherein the processor further loads a trigger table having a set of trigger dates based on the journey and triggers the message dispatch responsive to the set of trigger dates in the trigger table.

18. The system of claim 17, wherein the processor further receives a message start date and receiving an initialization message from a patient mobile device to initiate the journey and to initialize the set of trigger dates in the trigger table.

19. The system of claim 16, wherein the processor further:

awaits the patient response for a late response duration;

categorizes the patient response if the patient response is received within the late response duration;

sends a duplicate message if the patient response is not received within the late response duration; and flags the patient response as non-responsive if the patient response to the duplicate message is not received within a second late response duration.

* * * * *